(12) United States Patent
Nearing et al.

(10) Patent No.: US 6,169,919 B1
(45) Date of Patent: Jan. 2, 2001

(54) SYSTEM AND METHOD FOR QUANTIFYING ALTERNATION IN AN ELECTROCARDIOGRAM SIGNAL

(75) Inventors: Bruce D. Nearing, North Reading; Richard L. Verrier, Wellesley, both of MA (US)

(73) Assignee: Beth Israel Deaconess Medical Center, Inc., Boston, MA (US)

( * ) Notice: Under 35 U.S.C. 154(b), the term of this patent shall be extended for 0 days.

(21) Appl. No.: 09/335,680

(22) Filed: Jun. 18, 1999

Related U.S. Application Data
(60) Provisional application No. 60/132,806, filed on May 6, 1999.

(51) Int. Cl.7 .................................................. A61B 5/0452
(52) U.S. Cl. ............................................................. 600/518
(58) Field of Search ..................... 600/509, 510, 600/511, 512, 513, 515, 516, 517, 518

(56) References Cited

U.S. PATENT DOCUMENTS

| | | | |
|---|---|---|---|
| 3,554,187 | 1/1971 | Glassner et al. | 128/2.06 |
| 3,759,248 | 9/1973 | Valiquette | 128/2.06 A |
| 3,858,034 | 12/1974 | Anderson | 235/151.3 |
| 4,124,894 | 11/1978 | Vick et al. | 364/417 |
| 4,170,992 | 10/1979 | Dillman | 128/702 |
| 4,679,144 | 7/1987 | Cox et al. | 364/417 |
| 4,732,157 | 3/1988 | Kaplan et al. | 128/696 |
| 4,796,638 | 1/1989 | Sasaki | 128/696 |
| 4,802,491 | 2/1989 | Cohen et al. | 128/702 |
| 4,924,875 | 5/1990 | Chamoun | 128/696 |
| 4,947,857 | 8/1990 | Albert et al. | 128/696 |
| 5,020,540 | 6/1991 | Chamoun | 128/696 |
| 5,092,341 | 3/1992 | Kelen | 128/702 |
| 5,109,862 | 5/1992 | Kelen et al. | 128/702 |
| 5,148,812 | 9/1992 | Verrier et al. | 128/696 |
| 5,265,617 | 11/1993 | Verrier et al. | 128/704 |
| 5,437,285 | 8/1995 | Verrier et al. | 128/702 |
| 5,560,370 | 10/1996 | Verrier et al. | 128/705 |
| 5,842,997 | 12/1998 | Verrier et al. | 600/518 |
| 5,902,250 | 5/1999 | Waxman et al. | 600/515 |
| 5,921,940 | 7/1999 | Verrier et al. | 600/518 |

FOREIGN PATENT DOCUMENTS

| | | | | |
|---|---|---|---|---|
| WO 94/06350 A1 | 3/1994 | (WO) | ........................... | A61B/5/0452 |
| WO 95/15116 A1 | 6/1995 | (WO) | ........................... | A61B/5/0452 |

OTHER PUBLICATIONS

Adam, Dan R. et al., "Fluctuations in T–Wave Morphology and Susceptibility to Ventricular Fibrillation," *J. Electrocardiology*, vol. 17, No. 3, 1984, pp. 209–218.

Adam, Dan R. et al., "Ventricular Fibrillation And Fluctuations In The Magnitude Of The Repolarization Vector," *Computers in Cardiology*, 1982, pp. 241–244.

(List continued on next page.)

*Primary Examiner*—Scott M. Getzow
(74) *Attorney, Agent, or Firm*—Sterne, Kessler, Goldstein & Fox P.L.L.C.

(57) ABSTRACT

A system and method for quantifying alternation in the T-wave and ST segment of an ECG signal receives a digitized ECG signal (i.e., ECG data) for processing. The ECG data are used to calculate an odd median complex for the odd beats in the ECG data and an even median complex for the even beats in the ECG data. The odd median complex and the even median complex are then compared to obtain an estimate of the amplitude of beat-to-beat alternation in the ECG signal. Prior to calculation of the even and odd median complexes, the ECG data are filtered. Filtering of the ECG data involves low pass filtering the ECG data to remove high frequency noise, applying a baseline wander removal filter to the ECG data to remove low frequency artifacts, removing arrhythmic beats from the ECG data, and eliminating noisy beats from the ECG data. The filtered data are more suitable for calculation of an accurate estimate of alternation.

17 Claims, 10 Drawing Sheets

OTHER PUBLICATIONS

Adam, Dan R. et al., "Estimation of Ventricular Vulnerability To Fibrillation Through T–Wave Time Series Analysis," *Computers in Cardiology*, Sep. 1981, pp. 307–310.

Appel, Marvin L. et al., "Beat to Beat Variability in Cardiovascular Variables: Noise or Music?, " *JACC*, vol. 14, No. 5, Nov. 1, 1989, pp. 1139–1148.

Belic, N. and Garden, Julius M., "ECG Manifestations of Myocardial Ischemia," *Arch Inter Med.* vol. 140, Sep. 1980, pp. 1162–1165.

Doue, John C. and Vallance, Anthony G., "Computer–Aided ECG Analysis," *Hewlett–Packard Journal*, Sep. 36, 1985, pp. 29–34.

Goovaerts, H.G. et al., "A digital QRS detector based on the principle of contour Limiting, " *IEEE Transactions on Biomedical Engineering*, vol. BME–23, No. 2, Mar. 1976, pp. 154–160.

Joyal, Michael et al., "ST–Segment Alternans During Percutaneous Transluminal Coronary Angioplasty," Brief Reports from the Division of Cardiology, Department of Medicine, University of Florida and the Veterans Administration Medical Center, Gainesville, Florida, Jun. 8, 19884, pp. 915–916.

Laks, M.M et al., "ECG Computer Program Developed for a Retrospective and Prospective Study of the Pardee T Wave," *Computers in Cardiology*, Sep. 23–26, 1991, pp. 365–368.

Narayanaswamy S. et al., "Selective Beat Signal Averaging and Spectral Analysis of Beat Intervals to Determine the Mechanisms of Premature Ventricular Contractions," May 9, 1993, pp. 81–84.

Nearing, Bruce D. et al., "Dynamic Tracking of Cardiac Vulnerability by Complex Demodulation of the T Wave," *Science*, vol. 252, Apr. 19, 1991, pp. 437–440.

Nearing Bruce D. and Verrier, Richard L., "Simultaneous Assessment of Autonomic Regulation and Cardiac Vulnerability During Coronary Occlusion and Reperfusion by Complex Demodulation of heart Rate Variability and T–Wave Alternans," *Abstracts from the 65th Scientific Sessions: Suppplement to Circulation*, vol. 86, No. 4, Oct. 1992, p. 2541.

Raeder, Ernst A. et al., "Alternating Morphology Of The QRST Complex Preceding Sudden Death," *The New England Journal of Medicine*, Jan. 23, 1992, pp. 271–272.

Salerno, A. et al., "Ventricular arrhythmia during acute myocardial ischaemia in man. The role and significance of T–ST–T alternans and the prevention of ischaemic sudden death by medical treatment," *European Heart Journal*, vol. 7, Supplement A, 1986, pp. 63–75.

Schwartz, Peter J. and Malliani, Alberto, "Electrical alternation of the T–wave: Clinical and experimental evidence of its relationship with the sympathetic nervous system and with the long Q–T syndrome," *American Heart Journal*, vol. 89, No. 1, Jan., 1975, pp. 45–50.

Schwartz, Peter J., "Idiopathic Long QT syndrome: Progress and questions," *American Heart Journal*, Feb. 1985, pp. 399–411.

Sim, L.H. and Davies, J.A., A Microcomputer Based Signal Averaging System With Applications in Medicine,*Australasian Physical Sciences in Medicine*, vol. 2–6, No. 83, Aug. 1979, pp. 340–345.

Smith, Joseph M. et al., "Electrical alternans and cardiac electrical instability," *Circulation*, vol. 77, No. 1, Jan. 1988, pp. 110–121.

Smith, Joseph et al., "Subtle Alternating Electrocardiographic Morphology as an Indicator of Decreased Cardiac Electrical Stability," *Computers in Cardiology*, Sep. 8–11, 1985.

Speranza, G. et al., "Beat–to–beat measurement and analysis of the R–T interval in 24 h ECG Holter recordings," *Medical & Biological Engineering & Computing*, Sep. 1993, pp. 487–494.

Surawicz, B., "ST–segment, T–wave, and U–wave changes during myocardial ischemic and after myocardial infarction," *Canadian Journal of Cardiology*, Suppl. A:71A–84A, Jul. 1986.

Verrier, Richard L., "Method for Assessing Dispersion of Repolarization During Acute Myocardial Ischemia Without Cardiac Electrical Testing," *Abstracts from the 63rd Scientific Sessions: Supplement to Circulation*, vol. 82, No. 4, Oct. 1990.

SYSTEM AND METHOD FOR QUANTIFYING ALTERNATION IN AN ELECTROCARDIOGRAM SIGNAL

CROSS-REFERENCE TO RELATED APPLICATIONS

This application claims the benefit of U.S. Provisional Appl. No. 60/132,806, filed May 6, 1999.

STATEMENT AS TO RIGHTS TO INVENTIONS MADE UNDER FEDERALLY SPONSORED RESEARCH AND DEVELOPMENT

Part of the work performed during development of this invention utilized U.S. Government funds. The U.S. Government has certain rights in this invention.

BACKGROUND OF THE INVENTION

1. Field of the Invention

The invention relates to cardiology. More specifically, the invention relates to a system and method for calculating a magnitude of alternation in the T-waves of an electrocardiogram signal.

2. Background of the Invention

There is a growing interest in identifying patients with T-wave alternans as this has been shown to be a marker of electrical instability. For example, U.S. Pat. No. 5,148,812 to Richard L. Verrier and Bruce D. Nearing, the full text of which is incorporated herein by reference as if reproduced in full below, describes a method for non-invasive dynamic tracking of cardiac vulnerability to ventricular fibrillation by analysis of T-wave alternans. The '812 patent discloses a method for quantifying the magnitude of alternation in an electrocardiogram (ECG) signal that could be performed non-invasively during, for example, exercise stress testing.

The magnitude of alternans can, however, be difficult to accurately quantify. Alternans magnitudes are typically in the range of several microvolts to several hundred microvolts. These small amplitudes make the measurement and analysis of the alternans susceptible to noise. Noise sources such as white noise, motion artifacts caused by respiration or patient movement, noisy heart beats, premature beats and the like can skew alternans measurements. The inventors have therefore sought to improve upon the conventional methods for quantifying alternans.

SUMMARY OF THE INVENTION

The invention is a system and method for quantifying alternation in the T-wave and ST segment of an ECG signal. In a preferred embodiment of the invention, a digitized ECG signal (i.e., ECG data) is received for processing. The ECG data are used to calculate an odd median complex for the odd beats in the ECG data and an even median complex for the even beats in the ECG data. The odd median complex is then compared with the even median complex to obtain an estimate of the amplitude of beat-to-beat alternation in the ECG signal.

Filtering of the ECG data involves low pass filtering the ECG data to remove high frequency noise, applying a baseline wander removal filter to the ECG data to remove low frequency artifacts, removing ventricular arrhythmias from the ECG data, and eliminating noisy beats from the ECG data. The filtered data are more suitable for use in calculating an accurate estimate of alternation.

The step of applying a baseline wander removal filter to the ECG data includes determining an isoelectric value at each of a first isoelectric point (point 1) in a first beat, a second isoelectric point (point 2) in a second beat, and a third isoelectric point (point 3) in a third beat of the ECG data; fitting a spline curve to the first three isoelectric values; subtracting the values of the spline curve from the corresponding values of the ECG data between the first isoelectric point and the second isoelectric point; subtracting the values of the spline curve from the corresponding values of the ECG data between the second isoelectric point and the third isoelectric point; determining an isoelectric value for a next isoelectric point (e.g., point 4) in a next beat of the ECG data; fitting a next spline curve to the next isoelectric value (e.g., point 4) and isoelectric values corresponding to a previous two consecutive isoelectric points (e.g., points 2 and 3); subtracting the values of the next spline curve from the corresponding values of the ECG data between the next isoelectric point (e.g., point 4) and the previous isoelectric point (e.g., point 3); and repeating the process until a desired plurality of beats (e.g., points 3, 4 and 5; then points 4, 5 and 6; and so on) in the ECG data have been processed to remove low frequency artifacts from the ECG data.

The step of eliminating noisy beats includes calculating a mean value of all samples within a selected portion of a selected beat of the ECG data, calculating a difference between the mean value and each sample within the selected portion of the selected beat, calculating an average of the absolute value of the differences, comparing the average to a threshold, identifying the selected beat as a noisy beat based on the comparison of the average to the threshold, and eliminating the noisy beat from the calculation of the odd and even median complexes.

The step of calculating an odd median complex proceeds as follows. A first array (representing the odd median complex) is initialized with a plurality of odd median complex values. A second array (representing the even median complex) is initialized with a plurality of even median complex values. The samples of an odd beat of the ECG data are compared to corresponding values in the first array and, based on the comparison, the values of the first array are adjusted as follows. If a sample of the odd beat exceeds the corresponding value of the first array by a first amount but by less than a second amount, then the corresponding value is incremented by the first amount. If a sample of the odd beat exceeds the corresponding value of the first array by the second amount or by greater than the second amount, then the corresponding value is incremented by the second amount. If a sample of the odd beat is less than the corresponding value of the first array by the first amount but not the second amount, then the corresponding value is decremented by the first amount. Finally, if a sample of the odd beat is less than the corresponding value of the first array by the second amount or by greater than the second amount, then the corresponding value is decremented by the second amount. This process is repeated for other odd beats desired to be included in the calculation. This same process is then followed for the second array using the even beats.

Once the odd median complex and the even median complex have been calculated, a difference between sample points of the odd median complex and sample points of the even median complex is calculated for the region of the T-wave to obtain the estimate of the magnitude of alternation. Preferably, the maximum difference between the two complexes in the region of the T-wave is used as the estimate of the magnitude of alternation.

If desired, the ECG data may be divided into time segments with an alternans estimate being calculated for each segment. For example, a measure of alternation may be calculated for a time segment representing 15 seconds of ECG data.

These and other features and advantages of the invention are described in detail below with reference to the figures in which like reference numbers indicate like elements. Also in the figures, the left most digit of each reference number corresponds to the figure in which the reference number is first used.

DETAILED DESCRIPTION OF THE PREFERRED EMBODIMENTS

The preferred embodiments of the invention are discussed in detail below. While specific configurations and arrangements are discussed, it should be understood that this is done for illustration purposes only. A person skilled in the art will recognize that other configurations and arrangements may be used without departing from the spirit and scope of the invention.

Figure 1:
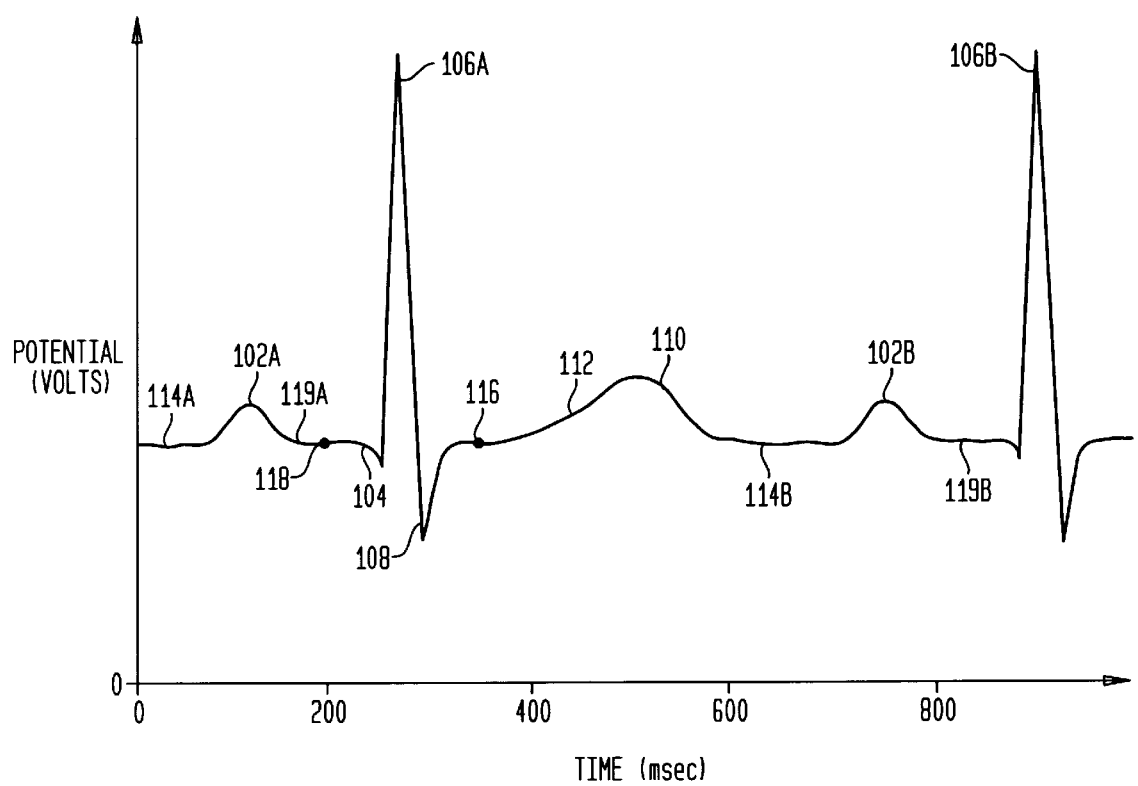
FIG. 1 is a typical ECG plot.

FIG. 1 shows a representative human surface ECG 100. A deflection 102 is known as the "P-wave" and is due to excitation of the atria. Deflections 104, 106 and 108 are known as the "Q-wave," "R-wave," and "S-wave," respectively, and result from excitation (de-polarization) of the ventricles. Deflection 110 is known as the "T-wave" and is due to recovery (repolarization) of the ventricles. One cycle (i.e., cardiac cycle or heart beat) of the ECG from the apex of a first R-wave 106A to the apex of a next R-wave 106B is known as the R-R or interbeat interval.

A portion 112 of ECG 100 between the end of S-wave 108 and the beginning of T-wave 110 is known as the "ST segment". Because this invention is concerned with alternans in the ST segment as well as in the T-wave, the term "T-wave" in this disclosure includes both the T-wave and the ST segment portions of the ECG.

Other interesting portions of ECG 100 include the TP segment, the PQ segment, the J point and the isoelectric value. The TP segment is the portion 114 of ECG 100 between the end of T-wave 110 and the beginning of P-wave 102. The PQ segment is the portion 119 of ECG 100 between the end of P wave 102 and the beginning of Q wave 104. The J point, indicated by point 116, marks the end of the QRS complex and is used to indicate the beginning of ST segment 112. The isoelectric value is represented by a point 118 selected on a flat portion of the PQ segment 119. However, the isoelectric value can also be represented by a point (not shown) selected on TP segment 114.

T-wave alternans or alternation is a regular beat-to-beat variation of the T-wave of an ECG which repeats itself every two beats and has been linked to underlying cardiac electrical instability. The inventors have found that most alternation occurs in the first half of the T-wave, the period of greatest vulnerability to ventricular fibrillation. See, Nearing BD, Huang AH and Verrier RL, "Dynamic Tracking of Cardiac Vulnerability by Complex Demodulation of the T Wave," Science 252:437–440, 1991.

Figure 2:
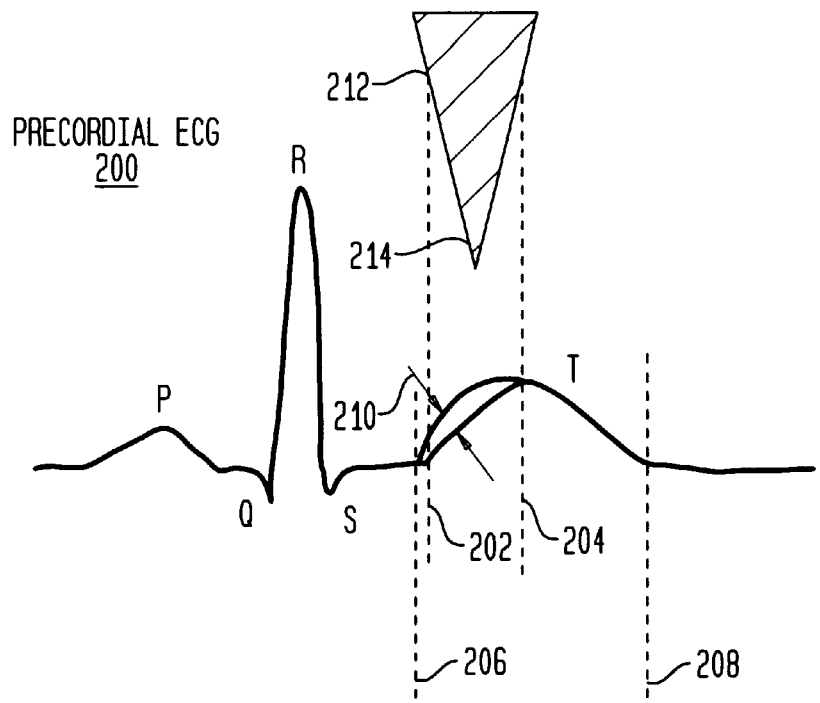
FIG. 2 is an ECG plot showing superimposition of several beats to illustrate T-wave alternation.

FIG. 2 illustrates the concept of T-wave alternation. A sample precordial ECG signal 200 is shown. In ECG 200, several beats have been superimposed upon one another to illustrate the alternans. Line 206 indicates the beginning of the T-wave, and line 208 indicates the end of the T-wave. The alternans is indicated at 210 as the divergence between the superimposed portions of the T-waves of successive beats. Note that the alternation occurs primarily during the first half of the T-wave as illustrated between lines 202,204. This is the period in which the heart is most vulnerable to cardiac electrical instability. This vulnerability is indicated by graph 212 which graphically depicts the amount of current required to induce ventricular fibrillation. Note that the vulnerability is maximum at the time corresponding to point 214 in graph 212. Point 214 indicates that a minimum amount of current will induce ventricular fibrillation at this point in the vulnerable period. A more detailed discussion of ECG sensing and analysis is provided in Dale Dubin, Rapid Interpretation of EKG's, 4th Edition, Cover Publishing Company, 1990, which is incorporated herein by reference.

Figure 3:
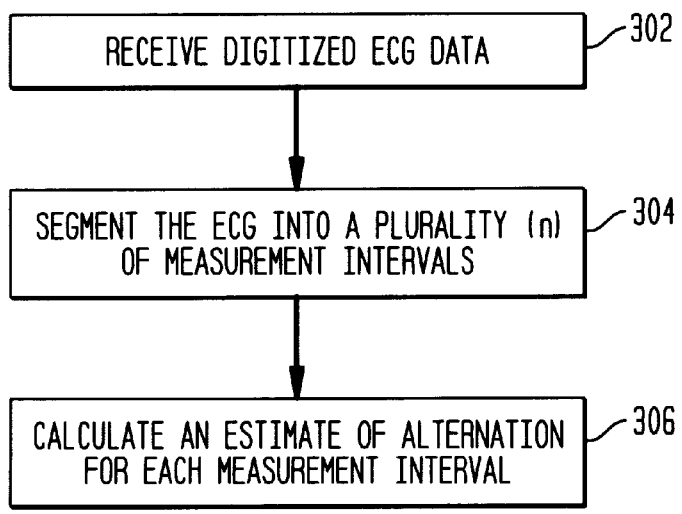
FIG. 3 is a flow chart illustrating the method of the invention.

A preferred embodiment of an alternans quantification method 300 according to the invention is illustrated in FIG. 3. In a first step 302, a digitized ECG signal is received for processing. For ease of reference, the digitized ECG signal will be referred to herein as ECG data. In a step 304, the ECG data are segmented into a plurality (n) of measurement intervals. For example, if the ECG data represent an ECG measurement taken from a patient over a time period of 10 minutes, the 10 minute long signal may be broken into smaller segments (e.g., 15 seconds) for processing. Alternatively, the entire set of 10 minutes of ECG data may be treated as a single segment. Finally, in a step 306, an estimate of alternation is calculated for each measurement interval or segment.

Figure 4:
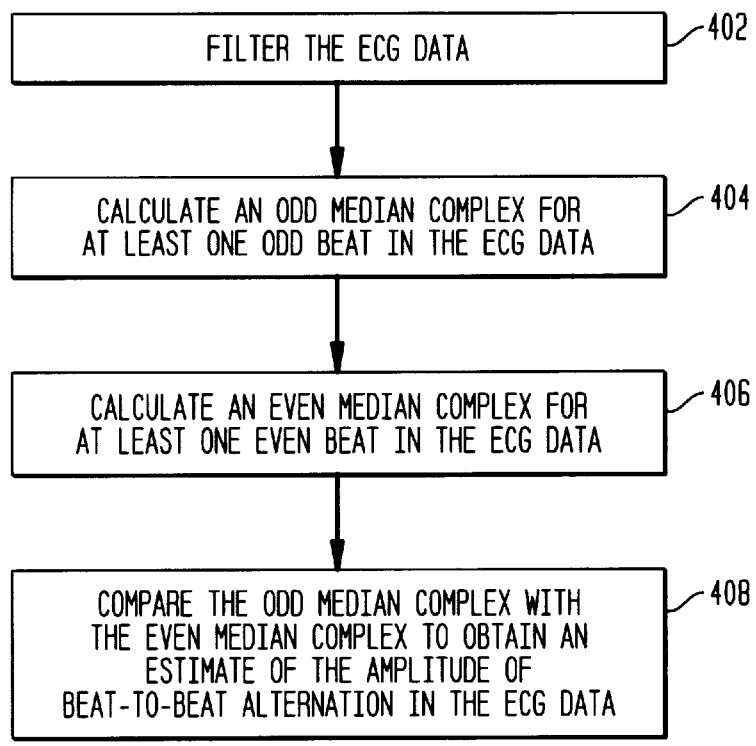
FIG. 4 is a flow chart illustrating the method of calculating an estimate of alternation in accordance with the present invention.

Step 306 of calculating an estimate of alternation is discussed in further detail with reference to FIG. 4. In a step 402, the ECG data are digitally filtered. As described in further detail below, the digital filtering removes, for example, high frequency noise, premature beats, noisy beats, and artifacts due to respiration and movement by the patient. In a step 404, an odd median complex is calculated for at least one odd beat in the ECG data. In a step 406, an even median complex is calculated for at least one even beat in the ECG data. Finally, in a step 408, the odd and even median complexes are compared to obtain an estimate of the amplitude of beat to beat alternation in the ECG data. Each of these steps of FIG. 4 is discussed in further detail below.

As used herein, the term "median complex" refers to a median representation of one or more beats of the ECG data. While the median complex can represent only a single beat, it is preferred that a larger number of beats contribute to the median values of the complex. The resultant median complex represents an average of the samples of the beats (odd or even) which contribute to it. However, in a preferred embodiment, the median complex is not a true average because the averaging is done so that the effect that any one beat can have on the median complex is limited. This prevents a spurious beat from skewing (i.e., adversely affecting) the accuracy of the median complex. How this is accomplished in the preferred embodiment of the invention is described below with reference to FIG. 8.

Figure 5:
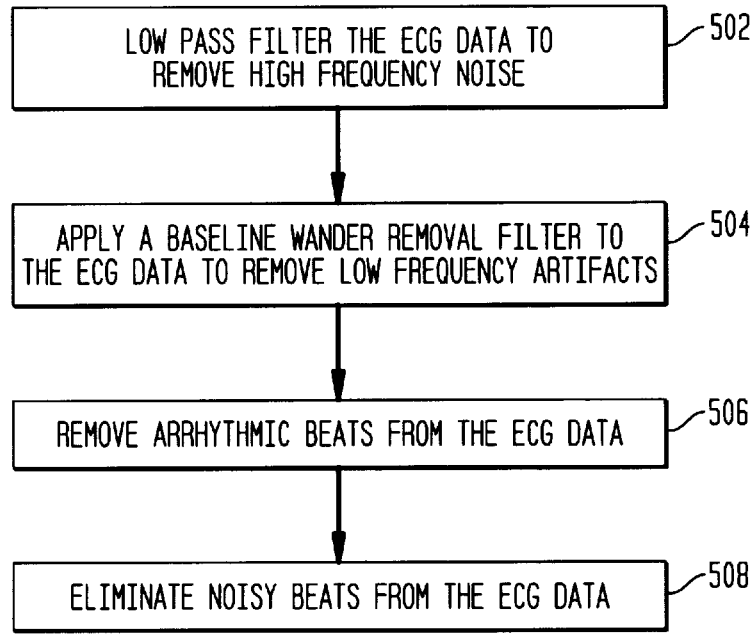
FIG. 5 is a flow chart illustrating filtering of ECG data in accordance with the present invention.

Filtering step 402 is described in additional detail with reference to FIG. 5. FIG. 5 depicts a low pass filtering step 502, a baseline wander removal step 504, a ventricular arrhythmia removal step 506 and a step 508 of eliminating noisy beats. In a preferred embodiment, each of these independent filtering steps is performed on the ECG data prior to the data being used to calculate the median complexes of steps 404 and 406. However, a person skilled in the art will recognize that one or more of the steps may be eliminated if desired. A person skilled in the art will also recognize that these steps may be performed in a different order as desired.

In step 502, the ECG data are low pass filtered to remove high frequency noise. In a preferred embodiment, an eighth order Butterworth filter having a corner frequency of 40 Hz is used. In step 504, a baseline wander removal filter is applied to the ECG data to remove low frequency artifacts. Examples of low frequency artifacts include artifacts caused by patient respiration as well as patient movement during, for example, exercise stress testing on a treadmill or exercise bicycle.

Figure 6:
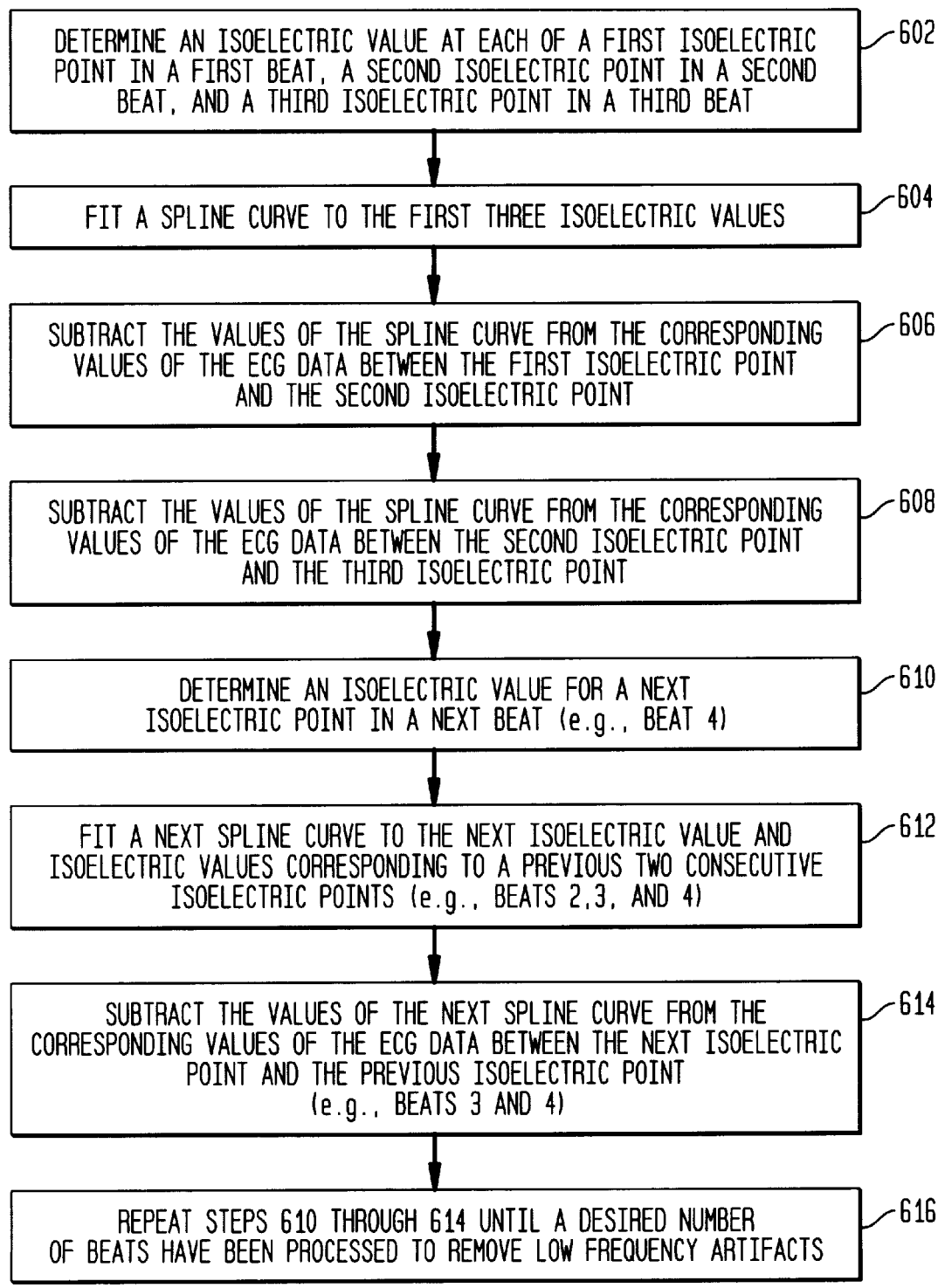
FIG. 6 is a flow chart illustrating the method of baseline wander removal in accordance with the present invention.

Operation of the baseline wander removal filter is described with reference to FIG. 6. In a step 602, an isoelectric value is determined for the first three beats in the ECG data. In a preferred embodiment, the isoelectric point is selected in the PQ segment of a beat. For example, the isoelectric point is selected as a point occurring 56 ms before the apex of the R-wave (the R-wave is generally used as a reference for locating other portions of the beat complex because its large amplitude permits it to be easily identified). In alternate embodiments, the isoelectric point may be selected in the TP segment. In either case, the points may be moved by a user upon visual inspection of the ECG data to achieve desired results. Such manual adjustment may be made once for each measurement interval.

Step 602 produces three data points, one isoelectric value from each of the first three beats. In a step 604, a spline curve is fit to the three isoelectric values corresponding to the three isoelectric points. In this preferred embodiment, a cubic spline curve is used. However, if isoelectric data from additional beats is used, higher order splines may be used. Further, more than one point per beat could be used to fit the spline. For example, two points per beat could be used; one point from the PQ segment and one point from the TP segment.

In a step 606, the values of the spline curve are subtracted from the corresponding values of the ECG data between the first and second isoelectric points (i.e., the ECG data lying between the first and second isoelectric points). In a step 608, the values of the spline curve are subtracted from the corresponding values of the ECG data for the portion of the ECG data between the second and third isoelectric points. This has the effect of removing wander from the isoelectric baseline of the ECG signal for the first three beats of the ECG data.

In a step 610, an isoelectric value is determined for an isoelectric point in a next beat. For example, the isoelectric value is determined for the fourth beat in the ECG data. In a step 612, a spline curve is fit to the second, third and fourth isoelectric values. In a step 614, the values of the spline curve determined in step 612 are subtracted from the ECG data for the portions of the ECG lying between the third and fourth isoelectric points. In a step 616, steps 610 through 614 are repeated for subsequent beats (e.g., the next three beats to be processed will be beats 3, 4 and 5; and then beats 4, 5 and 6; and so on) until all desired beats (e.g., all beats in the desired ECG segment) are processed to remove the low frequency artifacts affecting the isoelectric baseline.

The result of the baseline wander removal filtering of step 504 is to normalize the ECG data to a common isoelectric baseline.

Referring back to FIG. 5, step 506 removes ventricular arrhythmias from the ECG data. Examples of ventricular arrhythmias include premature beats, couplets, triplets, and ventricular tachycardia. These are beats that are not initiated through the normal conduction system of the heart. A normal, healthy heart may have a few such arrhythmias per hour while a diseased heart may have a much larger number. It is preferred to identify such beats so that they do not skew the alternans calculations. Ventricular arrhythmias are typically identified based on a comparison of the R-R intervals of the beats. For example, at a heart rate of 60 beats per minute, the R-R interval of a normal beat would be one second while an arrhythmic beat might have an R-R interval of only 0.6 seconds. Arrhythmic beats may also be identified based on the shape of the R-wave.

Once identified, arrhythmic beats can be eliminated from the ECG data or may be ignored during further processing of the ECG data.

Figure 7:
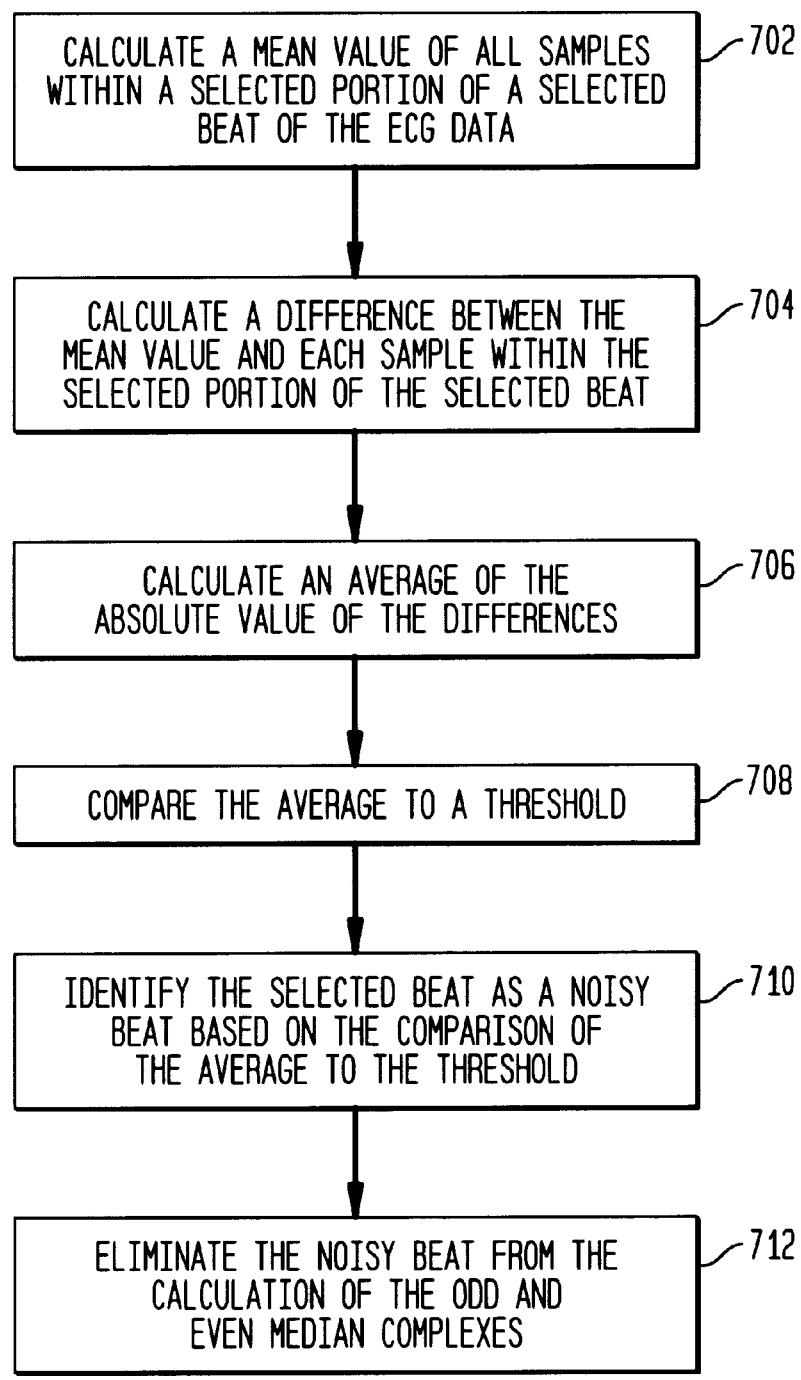
FIG. 7 is a flow chart illustrating the method of filtering the ECG data in accordance with the present invention to remove noisy beats.

In step 508, noisy beats are eliminated from the ECG data. Noisy beat removal is described in further detail with reference to FIG. 7. It is preferred that each beat in the ECG data segment be analyzed to determine whether it is a noisy beat. Noisy beats are eliminated from further processing so that they do not skew the alternans calculations. Determination of whether a beat is noisy proceeds as follows. In a step 702, a mean value is calculated for all samples within a selected portion of a beat. In a preferred embodiment, the selected portion is the TP segment of the beat. The location of the TP segment of each beat is determined based on the apex of the R-wave. In a preferred embodiment, the TP segment is estimated as the portion of the beat occurring in the region between 0.5 and 0.7 of the R-R interval. For example, given a heart rate of 60 beats per minute, one beat occurs every second so that the R-R interval is 1.0 second long. In this case, the TP segment would be estimated as occurring in the region between 0.5 and 0.7 seconds after the apex of the first R-wave. The mean value is determined for the TP segment by averaging together the samples of the ECG data located within the TP segment.

In an alternate embodiment, the TP segment may be set manually by the user during visual inspection of the ECG data. Furthermore, if desired by a user, this step of eliminating noisy beats may be skipped.

In a step 704, each sample of the TP segment is compared to this mean value. In a step 706, an average of the absolute values of the differences calculated in step 704 is computed for the samples of the TP segment. Alternatively, a standard deviation or variance of the samples of the TP segment can be calculated. In a step 708, the average is compared to a threshold. For example, a threshold of 50 $\mu$V is used in a preferred embodiment of the invention. Thus, if the average of the absolute value of the differences between each sample in the TP segment and the mean is greater than 50 μV, then the beat is classified as a noisy beat as indicated in step 710. Step 712 indicates that noisy beats are not used in the calculation of the odd and even median complexes in steps 404 and 406 of FIG. 4.

Figure 8:
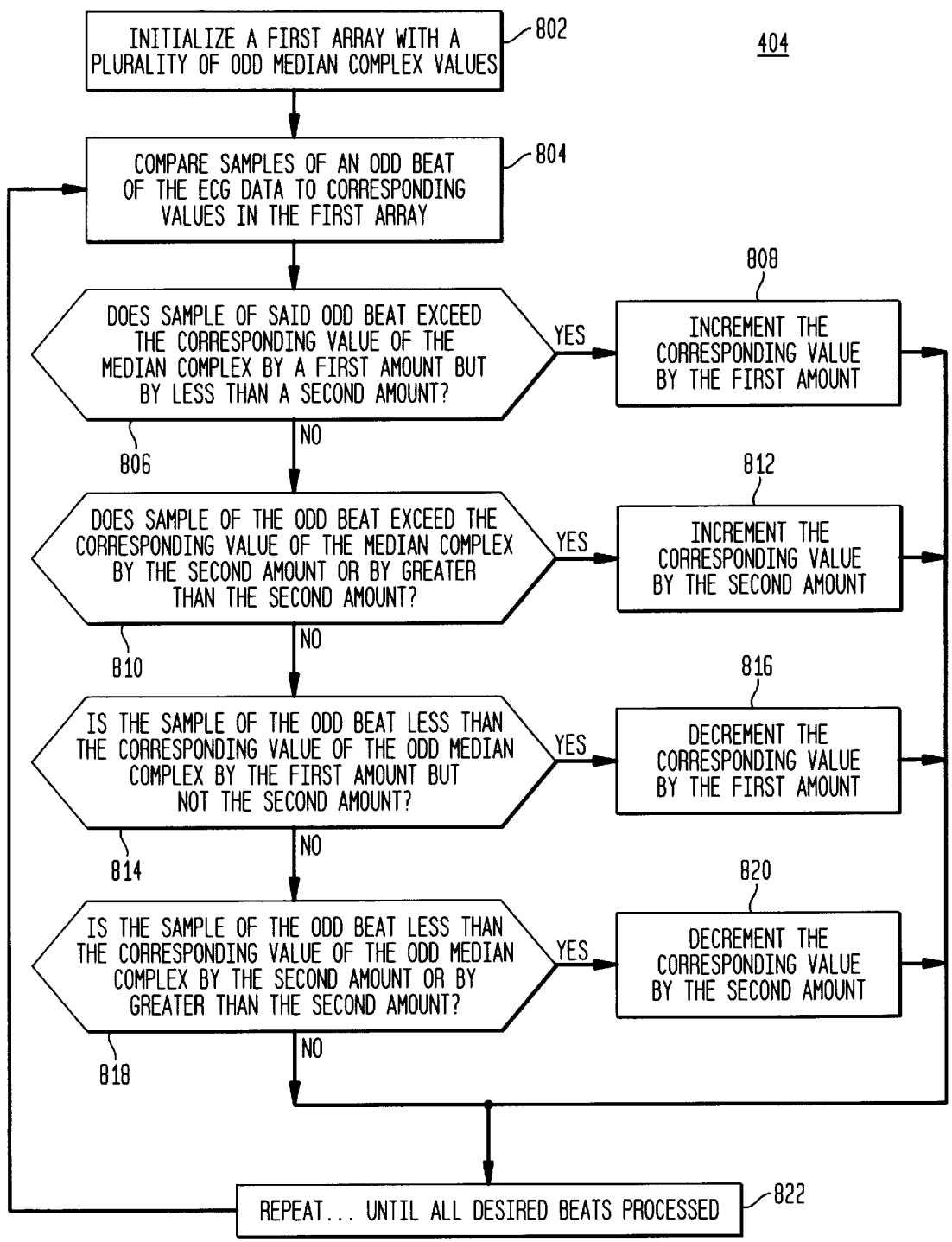
FIG. 8 is a flow chart illustrating calculation of a median complex in accordance with the present invention.

Referring back to FIG. 4, the filtered ECG data are used to calculate the odd median complex and the even median complex in steps 404 and 406. Step 404 of calculating an odd median complex is described in further detail with reference to FIG. 8. While the method of FIG. 8 is described in terms of calculating an odd median complex, a person skilled in the art will recognize that the method for calculating an even median complex is identical to that of calculating an odd median complex with the substitution of even beats for the odd beats.

In a step 802, a first array is initialized with a plurality of odd median complex values. For example, the samples of the first beat of the ECG data may be used as the initial values of the odd median complex. Alternatively, if a previous ECG segment (see step 304 of FIG. 3) has been processed, the odd median values resulting from that calculation may be used as the initial odd median values in step 802. In a step 804, the next odd beat of the ECG data are compared sample by sample to the odd median complex. Each odd beat (i.e., beats 1, 3, 5, 7, 9 and so on) is identified based on the apex of the R-wave. In a preferred embodiment, a beat is identified as the ECG data occurring between a point 450 msec before the apex of the R-wave to a point 550 msec after the apex of the R-wave for a total of 1.0 seconds of ECG data. At a sampling rate of 128 Hz, this equals 128 samples per beat. Thus, if the first beat is used to initialized the odd median complex, then 128 samples representing the third beat (i.e., the next odd beat) will be compared to the corresponding 128 samples in the odd median complex.

For each sample of an odd beat that is compared to a corresponding sample in the odd median complex, the result of the comparison is tested in steps 806 through 820. In step 806, if the sample of the current beat exceeds the corresponding value of the median complex by a first predetermined amount but by less than a second predetermined amount, then the corresponding value of the median complex is incremented by the first predetermined amount. This is indicated in step 808. In step 810, if the sample of the current odd beat exceeds the corresponding value of the odd median complex by the second amount or by more than the second amount, then, in step 812, the corresponding value in the odd median complex is incremented by the second amount.

Steps 814–820 parallel steps 806–812 but deal with the case where the sample of the current beat is less than the corresponding value of the median complex. That is, if the sample of the current beat is less than the corresponding value of the median complex by the predetermined amount but not by less than the second predetermined amount (see step 814), then the corresponding value of the median complex is decremented by the first predetermined amount (see step 816). If the sample of the current odd beat is less than the corresponding value of the odd median complex by the second amount or by more than the second amount (see step 818), then the corresponding value in the odd median complex is decremented by the second amount (see step 820).

As indicated in step 822, steps 804 through 818 are repeated for each sample of each odd beat until the desired number of odd beats (i.e., at least one) are processed. The resultant odd median complex represents an average of the samples of the odd beats. However, the averaging is done is such a way that the effect that any one beat can have on the median complex is limited to no more than the second amount. This prevents a spurious beat from skewing (i.e., adversely affecting) the accuracy of the median complex. In a preferred embodiment, the first amount is equal to one half of the second amount. For example, the first amount is selected as being equal to one sample level of the digitized ECG signal. Given a 10-bit analog to digital converter (ADC) and a maximum signal amplitude in the range of −2.5 mV to +2.5 mV, the ADC will have a resolution of 4.88 μV per sample level. Thus, the first value will be 4.88 μV and the second value will be 9.76 μV.

In this preferred embodiment, the difference between each sample of a beat and the median beat complex is compared to first and second amounts. In an alternate embodiment of the invention, the median beat complex can simply be incremented by the first amount if the sample exceeds the median complex and decremented by the first amount if the sample is less than the median complex. In another alternate embodiment, the difference between each sample of a beat and the median beat complex can be compared to more than two threshold amounts (e.g., three, four or more) having corresponding increment/decrement values.

Once the odd median complex and the even median complex are computed, they are compared in step 408 (see FIG. 4) to obtain an estimate of the amplitude of beat to beat alternation in the ECG data. In a preferred embodiment of the invention, the comparison involves determining the maximum difference between the corresponding values of the odd median complex and the even median complex in the region of the beat between the J point and the end of the T-wave. The J point is defined as a point marking the end of the QRS complex and is used to indicate the beginning of the ST segment. In a preferred embodiment of the invention, the J point is initially defined to be a point occurring 56 ms after the apex of the R-wave. The end of the T-wave is initially defined as a point occurring t milliseconds after the apex of the R-wave, where t is determined by the following equation:

$$t = 505 - 1.878\, HR + 0.0026\, HR^2$$

Where "HR" is heart rate expressed in beats per second, and "t" is expressed in ms (milliseconds).

These initial values for the J point and the end of the T-wave are estimates. The initial value for the J point is preferably then displayed to a user as a cursor superimposed on a sample beat (or on an average beat) from the measurement interval to permit manual user adjustment, as required. The J point may be adjusted once for the entire run of the measurement interval.

The end of the T-wave is calculated for each beat based on the equation set forth above. This equation sets the end of T-wave point slightly beyond where the actual end of the T-wave is expected to occur. This assures that the entire T-wave will be captured. The end of the T-wave may be displayed as a cursor on the sample beat for inspection by a user.

Note that, for the first measurement interval, the odd beats are beats 1, 3, 5, 7 . . . to the end of the measurement interval. Similarly, the even beats for the first measurement interval are 2, 4, 6, 8 . . . to the end of the measurement interval. For all subsequent measurement intervals, if the last beat of the immediately preceding measurement interval was EVEN, the odd beats will be beats 1, 3, 5, 7, etc. and the even beats will be beats 2, 4, 6, 8 etc. However, if the last beat of the immediately preceding measurement interval was ODD, then the odd beats will be beats 2, 4, 6, 8, etc. and the even beats will be beats 1, 3, 5, 7, etc. This later rule preserves the relative groupings of odd and even beats throughout an ECG data file as the method proceeds from one measurement interval to the next.

The method of the invention can also be used to quantify alternation during atrial repolarization. That is, just as alternans occurs during ventricular repolarization, an alternation pattern can also be sensed during repolarization of the atria. The alternans in the atrial T-wave indicates electrical instability during atrial repolarization and heralds atrial fibrillation.

Figure 9:
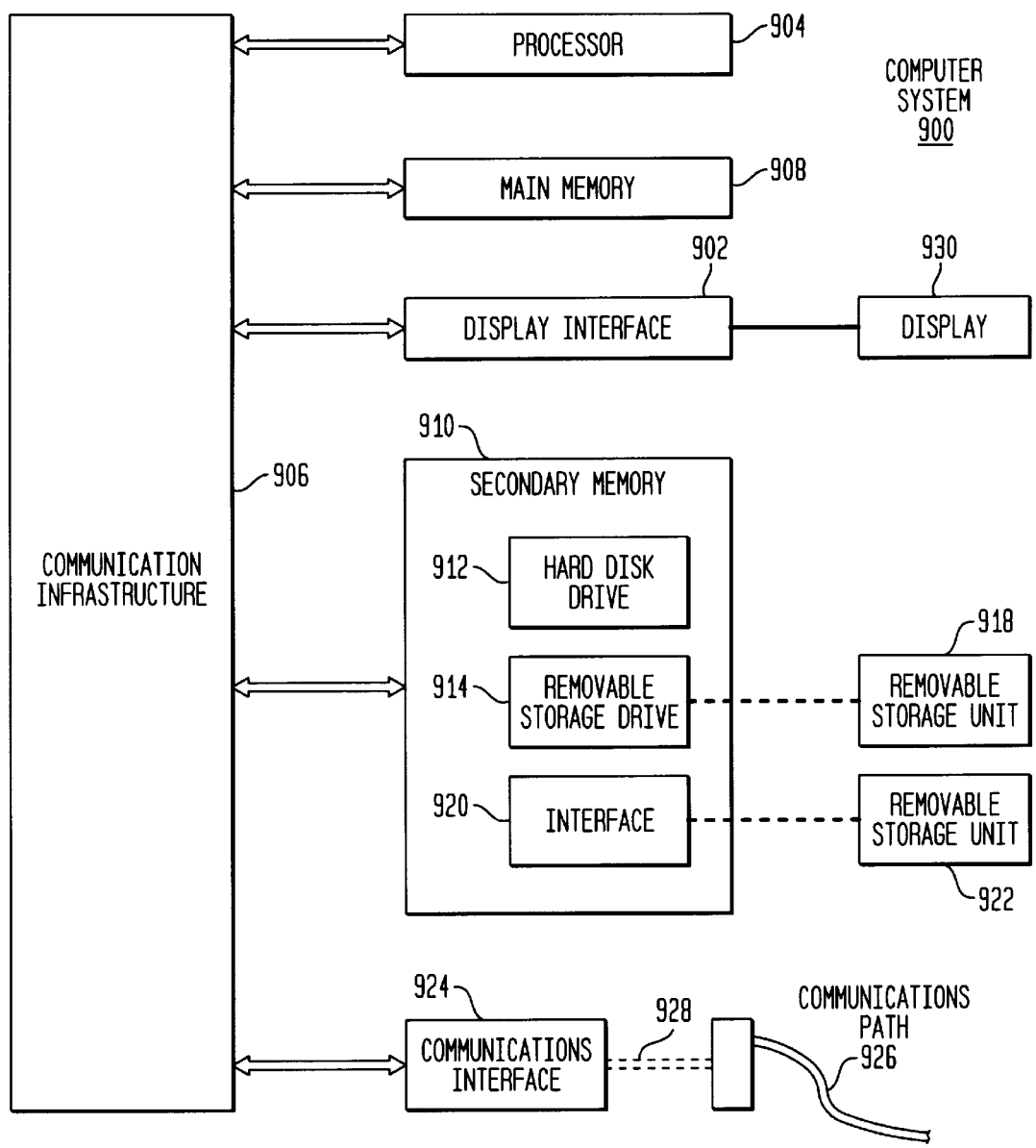
FIG. 9 is a block diagram of a computer system for implementation of the present invention.

The method of the invention may be implemented using hardware, software or a combination thereof and may be implemented in one or more computer systems or other processing systems. In an example embodiment, the invention was implemented in software running on a general purpose computer 900 as illustrated in FIG. 9. Computer system 900 includes one or more processors, such as processor 904. Processor 904 is connected to a communication infrastructure 906 (e.g., a communications bus, cross-over bar, or network). Computer system 900 includes a display interface 902 that forwards graphics, text, and other data from the communication infrastructure 906 (or from a frame buffer not shown) for display on the display unit 930.

Computer system 900 also includes a main memory 908, preferably random access memory (RAM), and may also include a secondary memory 910. The secondary memory 910 may include, for example, a hard disk drive 912 and/or a removable storage drive 914, representing a floppy disk drive, a magnetic tape drive, an optical disk drive, etc. The removable storage drive 914 reads from and/or writes to a removable storage unit 918 in a well known manner. Removable storage unit 918, represents a floppy disk, magnetic tape, optical disk, etc. which is read by and written to by removable storage drive 914. As will be appreciated, the removable storage unit 918 includes a computer usable storage medium having stored therein computer software and/or data.

In alternative embodiments, secondary memory 910 may include other means for allowing computer programs or other instructions to be loaded into computer system 900. Such means may include, for example, a removable storage unit 922 and an interface 920. Examples of such removable storage units/interfaces include a program cartridge and cartridge interface (such as that found in video game devices), a removable memory chip (such as a ROM, PROM, EPROM or EEPROM) and associated socket, and other removable storage units 922 and interfaces 920 which allow software and data to be transferred from the removable storage unit 922 to computer system 900.

Computer system 900 may also include a communications interface 924. Communications interface 924 allows software and data to be transferred between computer system 900 and external devices. Examples of communications interface 924 may include a modem, a network interface (such as an Ethernet card), a communications port, a PCMCIA slot and card, etc. Software and data transferred via communications interface 924 are in the form of signals 928 which may be electronic, electromagnetic, optical or other signals capable of being received by communications interface 924. Signals 928 are provided to communications interface 924 via a communications path (i.e., channel) 926. Channel 926 carries signals 928 and may be implemented using wire or cable, fiber optics, a phone line, a cellular phone link, an RF link and other communications channels.

In this document, the terms "computer program medium" and "computer usable medium" are used to generally refer to media such as removable storage drive 914, a hard disk installed in hard disk drive 912, and signals 928. These computer program products are means for providing software to computer system 900. The invention includes such computer program products.

Computer programs (also called computer control logic) are stored in main memory 908 and/or secondary memory 910. Computer programs may also be received via communications interface 924. Such computer programs, when executed, enable computer system 900 to perform the features of the present invention as discussed herein. In particular, the computer programs, when executed, enable processor 904 to perform the functions of the present invention. Accordingly, such computer programs represent controllers of computer system 900.

In an embodiment where the invention is implemented using software, the software may be stored in a computer program product and loaded into computer system 900 using removable storage drive 914, hard drive 912 or communications interface 924. The control logic (software), when executed by the processor 904, causes the processor 904 to perform the functions of the invention as described herein.

In another embodiment, the invention is implemented primarily in hardware using, for example, hardware components such as application specific integrated circuits (ASICs). Implementation of the hardware state machine to perform the functions described herein will be apparent to persons skilled in the relevant art(s).

In yet another embodiment, the invention is implemented using a combination of both hardware and software.

In an example software embodiment of the invention, the methods described above were implemented in the C++ programming language. The software was then loaded into computer system 900. In this embodiment, computer system 900 is a MARS-8000 Unity Workstation available from Marquette Medical Systems, Inc. (a GE Medical Systems Company), Milwaukee, Wis., USA. The MARS-8000 is a Sun Ultra-1 workstation configured with Marquette ECG analysis software. The MARS-8000 is equipped to receive ECG data in several different ways. These include receiving data via an Ethernet connection, from a Marquette DAT (i.e., magnetic tape for long term storage of Holter files) drive, from a Marquette tape acquisition unit configured to read tapes from a Marquette Holter recorder, and from a Marquette SEER acquisition unit configured to read flashcards from a SEER recorder. ECG data from other sources and in other formats can be reformatted into Marquette format and loaded into the MARS-8000 via the Ethernet connection.

Figure 10:
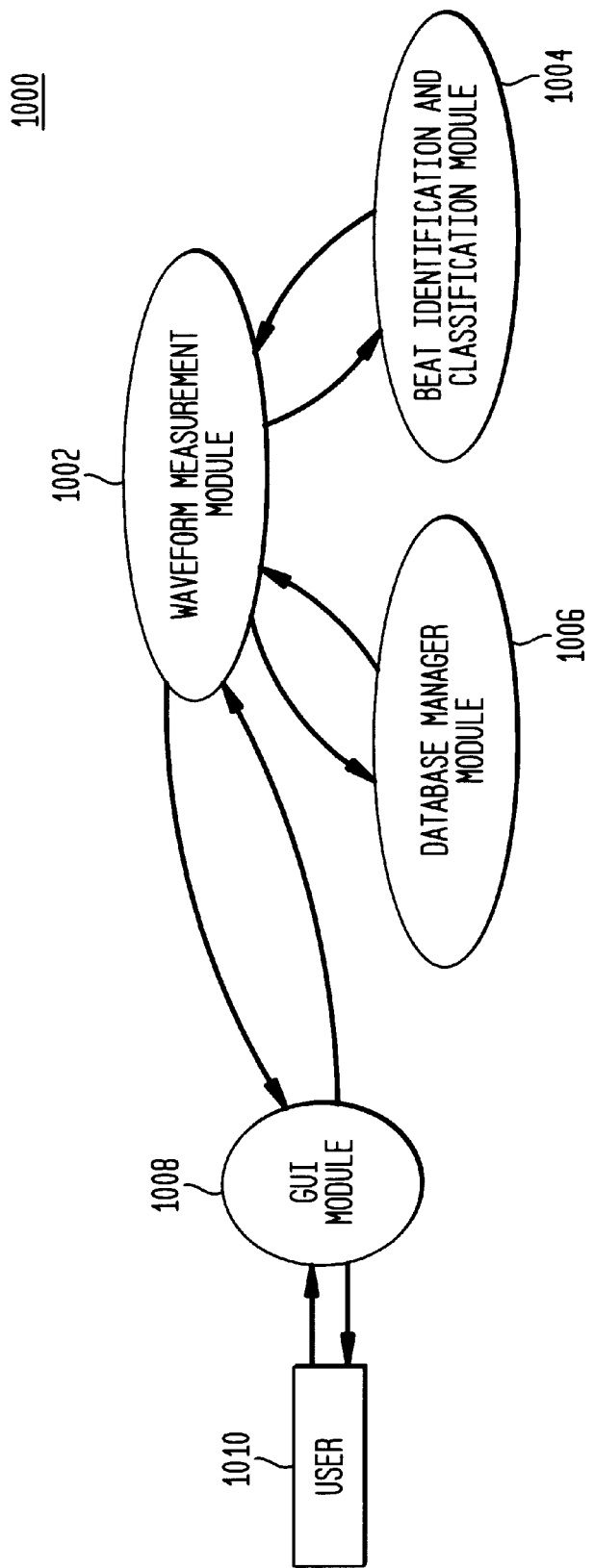
FIG. 10 is a functional block diagram of a computer software program implementation of the invention.

FIG. 10 is a functional block diagram illustrating the structure and operation of a computer software program 1000 for use with computer system 900. Program 1000 includes a waveform measurement module 1002, a beat identification and classification module 1004, a database manager module 1006 and a graphical user interface module (GUI) 1008. Database manager module 1006 manages receipt and storage of ECG data, and provides the raw ECG data to waveform measurement module 1002. Waveform measurement module 1002 in conjunction with beat identification and classification module 1004 performs the functions shown in the flowcharts of FIGS. 3–8 of filtering the raw ECG data and calculating an estimation of alternation. In these calculations, beat identification and classification module 1004 provides certain beat identification and classification information to waveform measurement module 1002 for use in the alternans calculations, including QRS position within the measurement interval and beat classification as either normal, supraventricular, ventricular or artifact (noise).

GUI module 1008 provides an interface with a user 1010. Waveform measurement module 1002 provides GUI module 1008 with the following information for display to user 1010: an alternans versus time graph; raw ECG data; a sample or median (e.g., odd and/or even) beat including the position of an isoelectric cursor, a J point cursor, and a TP segment cursor; an alternans value; a noise value; and a time of current measurement interval. GUI module 1008 controls display of this information to user 1010.

GUI module 1008 also receives input from user 1010 and provides the input to waveform measurement module 1002. User input includes: start/stop/reset signals indications; close/open display window; selection of parameters for the low pass filter (e.g., filter order N and cutoff frequency $f_c$), the baseline wander filter (e.g., extend filter to include additional data such as data from more than two beats or data from TP segment in addition to PQ segment), and the noisy beat filter (e.g., value of threshold, and beginning and end of portion of ECG used as the isoelectric); and adjustment of the isoelectric cursor, J point cursor and TP segment cursor. GUI module 1008 displays the various ECG data to user 1010 and allows user control of the alternans calculation process via filtering and data selection.

Figure 11A:
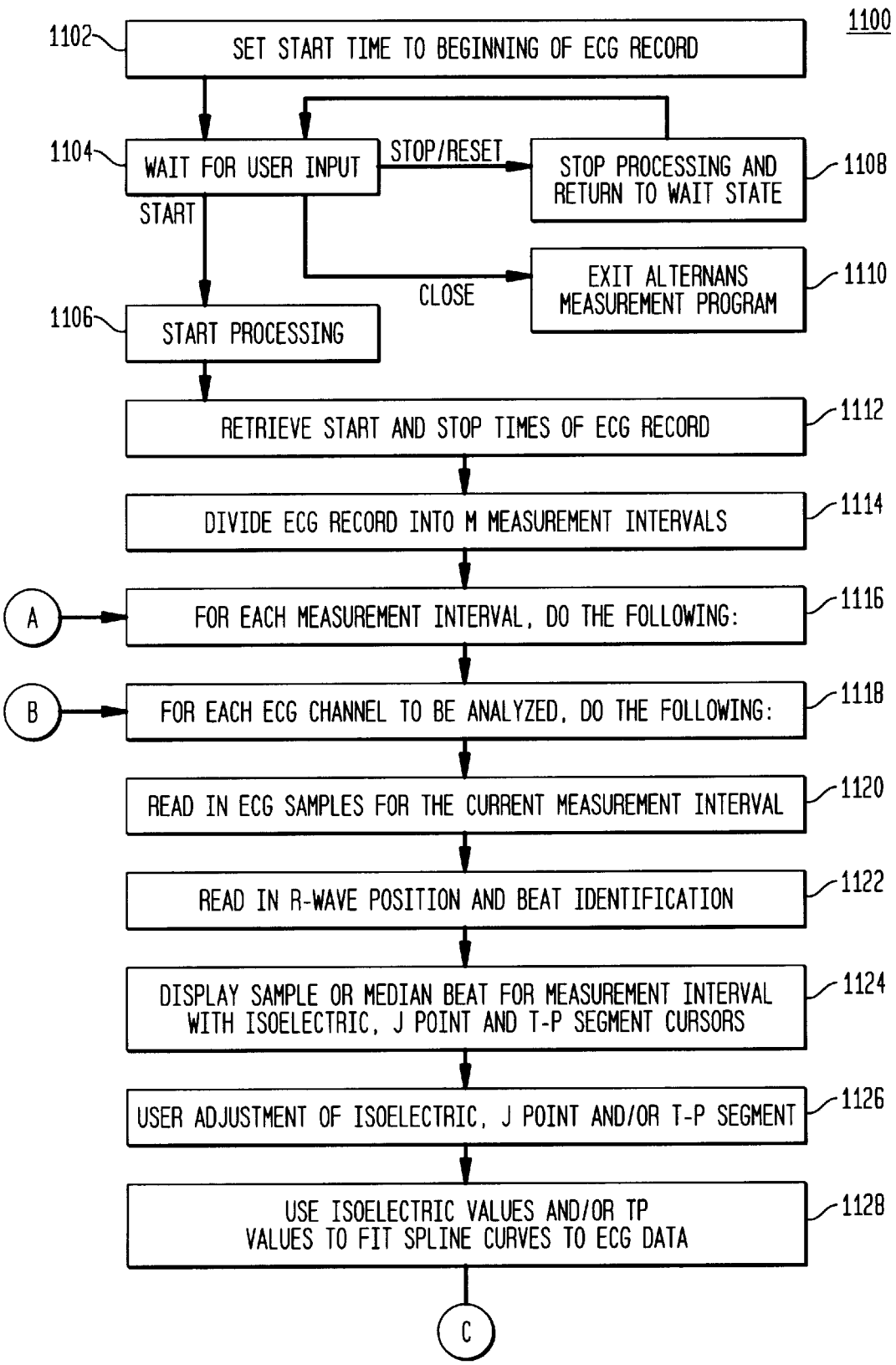
FIGS. 11A and 11B contain a flow chart of the steps performed by a waveform measurement module 1002 of FIG. 10.
Figure 11B:
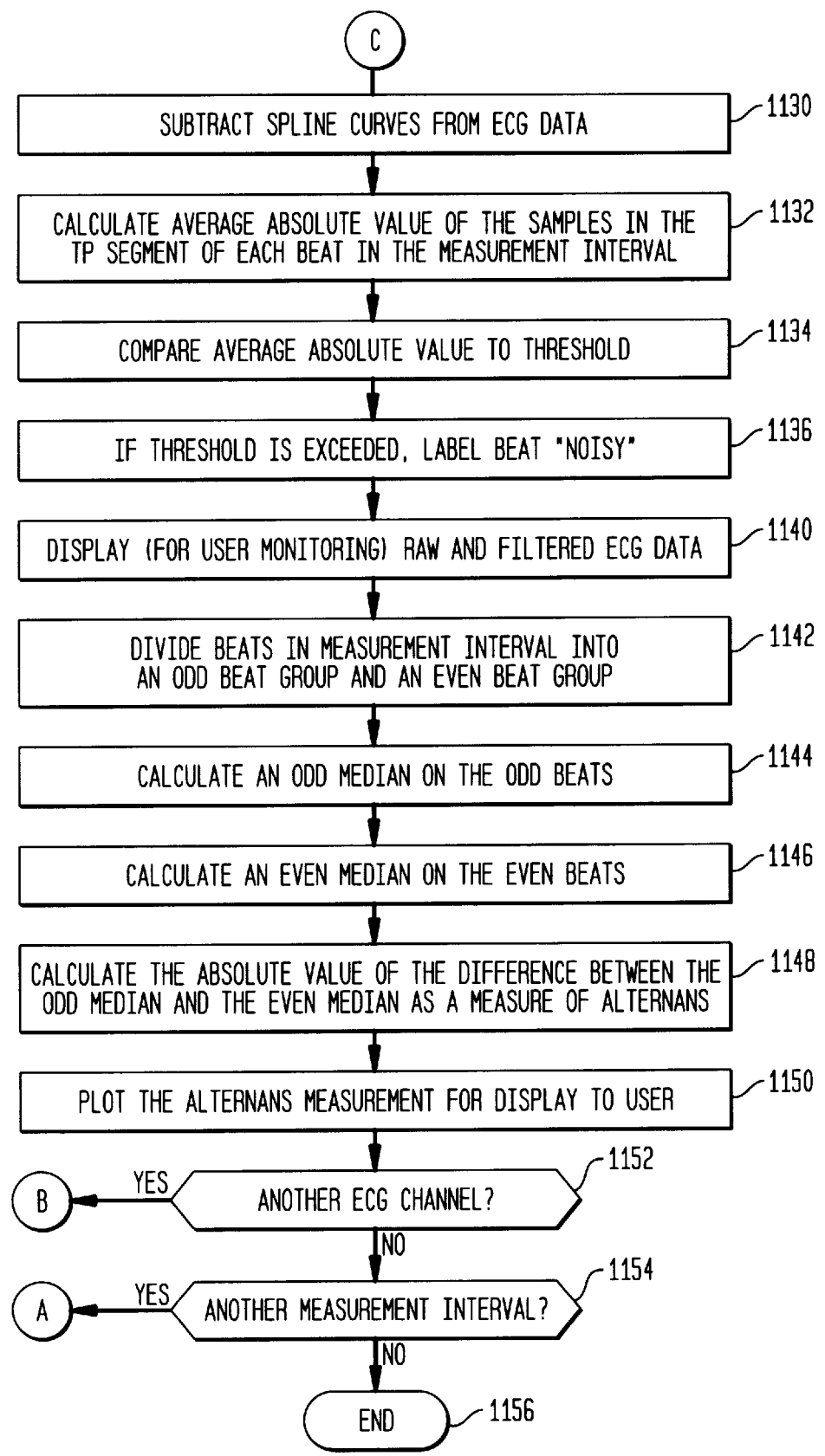

In this example implementation, the functionality of GUI module 1008, beat identification and classification module 1004 and database manager module 1006 are performed by the Marquette ECG analysis software of the MARS-8000 Unity workstation. However, it will be apparent to a personal skilled in the relevant art based on the foregoing disclosure how to implement this functionality in any number of programming languages. Also in this example implementation, the functionality of waveform measurement module 1002 is implemented in C++ code. A flow chart of the C++ implementation is shown in FIG. 11.

In a step 1102, a start time is set to the beginning of the ECG data record. In a step 1104, the system waits for user input. If the user inputs a "start" command, then the method proceeds to step 1106 where processing commences. If the user input is a "close" command, then the alternans measurement program is closed as indicated at step 1110. If the user input is a "stop" or "reset" command, then processing is stopped as indicated at 1108 and the method returns to step 1104 and continues to wait. However, stop and reset commands are treated differently. In the case of a stop command received during a measurement, the method returns to step 1104 but does not reset the current measurement interval to the beginning of the ECG record. This permits the process to be stopped but then resumed from the same point at which it was stopped. In the case of a reset command, the start time is reset to the beginning of the ECG record before returning to the wait state at step 1104.

Once processing is commenced as indicated at step 1106, the start and stop times for the ECG record are retrieved at step 1112. At step 1114, the ECG record is divided into M measurement intervals. As indicated at step 1116, steps 1118–1152 are repeated for each measurement interval. As indicated at 1118, steps 1120–1150 are repeated for each ECG channel to be analyzed.

At step 1120, ECG samples for the current measurement interval are received. At step 1122, the R-wave position and beat identification are received. At step 1124, the sample beat and the median beat are displayed for the measurement interval. An isoelectric cursor, a J point cursor and a TP segment cursor are also shown for the sample and median beats. Display to a user of the sample and median beats allows user adjustment of these cursors to adjust the isoelectric point, the J point and/or a point on the TP segment as indicated at step 1126. Thus, if the preset positions of these cursors is not ideal for a particular ECG data record, they can be adjusted during visual inspection of the sample and/or median beats.

At step 1128, the isoelectric values and/or the TP segment values are used to fit spline curves to the ECG data. At step 1130, the spline curves are subtracted from the ECG data to remove wander from the isoelectric baseline of the ECG signal. In step 1132, the average absolute value of the ECG samples in the TP segment of each beat in the measurement interval is calculated. At step 1134, the average absolute value is compared to a threshold. If the threshold is exceeded, the beat is indicated as a noisy beat at step 1136.

Next, the filtered ECG data and/or the raw ECG data is displayed to the user in a step 1140. In step 1142, the beats in a measurement interval are divided into an odd beat group and an even beat group. In step 1144, a median beat is calculated for the odd group of beats. In a step 1146, a median beat is calculated for the group of even beats. In a step 1148, the absolute value of the difference between the odd median beat and the even median beat is calculated as a measure of alternans. The noisy beats identified in step 1136 and the ventricular arrhythmias identified in step 1122 are not included in this calculation. In a step 1150, the alternans measurement is plotted for display to the user.

At step 1152, it is determined whether another ECG channel requires processing. If another ECG channel requires processing, then the method returns to step 1118. If no remaining ECG channels require processing, the method proceeds to step 1154 where it is determined whether processing is required for another measurement interval. If processing is required for another measurement interval, the method returns to step 1116. If no further measurement intervals require processing, the method ends at step 1156.

The inventors used the method of the present invention to measure T-wave alternans magnitude in 24-hour ambulatory ECG recordings from patients enrolled in the ATRAMI (Autonomic Tone and Reflexes After Myocardial Infarction) study housed at Columbia University School of Physicians and Surgeons. The ATRAMI study, described in La Rovere et al., "Baroreflex sensitivity and heart-rate variability in prediction of total cardiac mortality after myocardial infarction," *The Lancet,* Vol. 351, Feb. 14, 1998, pp. 478–484 (with commentary at pp. 461–2), the full text of which is incorporated herein by reference as if reproduced in full below, is a large prospective study based on 1284 post-myocardial infarction patients. A nested case-control epidemiologic approach was used with cases defined as patients who had died from an arrhythmic event during the follow-up period. The controls were matched for sex, age (+/−5 years), site of myocardial infarction, left ventricular ejection fraction (+/−3%) and thrombolytic treatment. Investigators blind to patient outcome conducted the ECG analysis. The ECG data were then filtered and processed according to the method of the present invention. Alternation was evaluated at maximum heart rate, maximum ST-segment depression and at 8:00 am. Measurement was made without controlling heart rate. Analysis of the first 14 cases and 25 controls revealed some differences only at the time of maximum heart rate: 106+−49 $\mu V$ versus 78 +−55 $\mu V$. Significantly more cases than controls (71% versus 32%, p=0.03) had alternans values greater than or equal to 80 $\mu V$. The estimated risk of arrhythmic death was 5.3 times higher (95% CI: 1.3–22.2) among patients with levels of T-wave alternans above this cutpoint. These preliminary results show promise with respect to the potential predictive value of alternans analysis in accordance with the present invention.

In another study the inventors analyzed data from patients enrolled in the Vascular Basis Study housed at Brigham & Women's Hospital and Harvard Medical School in Boston, Mass. Eighteen patients with stable coronary artery disease from the Vascular Basis study were evaluated for T-wave alternans during standard treadmill testing. Patients gave informed consent and were withdrawn from all anti-anginal medications for 4 days prior to performance of an exercise treadmill test using the ACIP protocol. ECGs were digitized at 500 Hz using a GE Marquette CardioSys treadmill and recorded with standard electrodes. BCGs were filtered at 50 Hz and the baseline wander artifact was removed in accordance with the present invention. The average exercise test duration was 9 min 3 sec +/−48 sec. ST-segment depression greater than 1.0 mm occurred in 15 of 18 patients. A stable, visible alternans pattern was easily identified during the stress test in 12 of 18 patients at a standard gain of 10 mm/mV. 11 patients had both alternans and ischemia. Of three patients without ST-segment depression, one had alternans. Alternans levels were estimated in accordance with the present invention and were verified by visual inspection. Alternans increased from resting baseline value of 11.9+/−0.8 $\mu$V to peak value of 103.4+/−8.6 $\mu$V (p less than 0.001) at 7 min 16 sec +/−44 sec during exercise. Heart rate increased from 67.3 +/−2.9 to 118.9+/−4.8 bpm (p less than 0.001) at the same time. This study shows that marked T-wave alternans can be consistently induced during standard treadmill exercise in patients with stable coronary artery disease without anti-ischemic medications. Measurement of the alternans can be made in accordance with the present invention without controlling heart rate. Moreover, ST-segment and T-wave alternans measure different endpoints, and therefore provide complementary information. The approach described permits further exploration of the pathophysiology of ischemia-induced cardiac electrical instability within the context of routine clinical testing.

In yet another study, the inventors analyzed data from patients participating in a study housed at Uniformed Services University of Health Sciences, Bethesda, Md. Investigators at Uniformed Services University of the Health Sciences in collaboration with the inventors monitored 11 male patients with coronary artery disease and implantable cardioverter defibrillators, aged 68±7 years, to assess whether T-wave alternans could be induced by mental stress or exercise. Patients performed standardized behavioral tests, namely mental arithmetic, anger recall, and bicycle exercise. T-wave alternans increased significantly during each intervention (p<0.001) and there was no ECG evidence of ischemia. While increases in alternans with exercise were greater than with mental stress, it was found that increased heart rate correlated with increases in alternans magnitude. Therefore, a rate correction feature was introduced, and T-wave alternans increases resulting from anger recall (p=0.001) and mental arithmetic (p=0.03) but not exercise (p=0.09) remained significant after this statistical adjustment was implemented.

These promising results indicate that the present invention is ideal for use in the real-time calculation of alternans. Such real-time applications include: calculation of alternans during ambulatory (Holter) heart monitoring; during exercise or behavioral stress testing; and calculation of alternans by an implanted cardioverter, pacemaker or other device to control administration of electrical or pharmacologic therapy. Furthermore, the method of the invention is not susceptible to variations in heart rate so that no pacing or other heart rate control is required. Of course, ECGs can also be stored for later analysis in accordance with the invention.

While the invention has been described in the environment of analyzing electrocardiogram signals, a person skilled in the art will recognize that the invention has applicability to the analysis and quantification of other types of electrophysiologic signals.

Furthermore, while the invention has been described and illustrated with a certain degree of particularity, it is understood that those skilled in the art will recognize a variety of applications and appropriate modifications within the spirit of the invention and the scope of the claims.

What is claimed is:

1. A method of quantifying alternation in an ECG signal having a plurality of beats, the method comprising the steps of:

(a) receiving digitized ECG data representing the ECG signal;

(b) calculating an odd median complex for at least one odd beat in said ECG data;

(c) calculating an even median complex for at least one even beat in said ECG data; and (d) comparing said odd median complex with said even median complex to obtain an estimate of the amplitude of beat-to-beat alternation in said ECG signal.

2. The method of claim 1, further comprising the step before step (b) of:

filtering said ECG data.

3. The method of claim 2, wherein said filtering step comprises:

low pass filtering said ECG data; and applying a baseline wander removal filter to said ECG data.

4. The method of claim 3, wherein said filtering step further comprises:

removing arrhythmic beats from said ECG data.

5. The method of claim 4, wherein said filtering step further comprises:

eliminating noisy beats from said ECG data.

6. The method of claim 5, wherein said eliminating step comprises:

calculating a mean value of all samples within a selected portion of a selected beat of said ECG data;

calculating a difference between said mean value and each sample within said selected portion of said selected beat;

calculating an average of the absolute value of said differences;

comparing said average to a threshold;

identifying said selected beat as a noisy beat based on said comparison of said average to said threshold; and eliminating said noisy beat from said calculation of said odd and even median complexes.

7. The method of claim 3, wherein said applying step comprises:

(i) determining an isoelectric value at each of a first isoelectric point in a first beat, a second isoelectric point in a second beat, and a third isoelectric point in a third beat of said ECG data;

(ii) fitting a spline curve to said first three isoelectric values;

(iii) subtracting the values of said spline curve from the corresponding values of said ECG data between said first isoelectric point and said second isoelectric point;

(iv) subtracting the values of said spline curve from the corresponding values of said ECG data between said second isoelectric point and said third isoelectric point;

(v) determining an isoelectric value for a next isoelectric point in a next beat of said ECG data;

(vi) fitting a next spline curve to said next isoelectric value and isoelectric values corresponding to a previous two consecutive isoelectric points;

(vii) subtracting the values of said next spline curve from the corresponding values of said ECG data between said next isoelectric point and said previous isoelectric point; and (viii) repeating steps (v) through (vii) until a desired plurality of beats in said ECG data have been processed to remove low frequency artifacts from said ECG data.

8. The method of claim 1, wherein step (d) comprises:
comparing a T-wave portion of said odd median complex with a T-wave portion of said even median complex to obtain an estimate of the amplitude of beat-to-beat alternation in said ECG signal.

9. The method of claim 1, wherein steps (a) through (d) are performed for a first plurality of beats of said ECG signal, and wherein said method further comprises:
repeating steps (a) through (d) for a second plurality of beats of said ECG signal to obtain a second estimate of the amplitude of beat-to-beat alternation in said ECG signal.

10. The method of claim 1, wherein step (b) comprises:

(i) initializing a first array with a plurality of odd median complex values, said first array representing said odd median complex;

(ii) initializing a second array with a plurality of even median complex values, said second array representing said even median complex;

(iii) comparing samples of an odd beat of said ECG data to corresponding values in said first array and adjusting said values of said first array as follows
  A. if a sample of said odd beat exceeds said corresponding value of said first array by a first amount but by less than a second amount, then incrementing said corresponding value by said first amount,
  B. if a sample of said odd beat exceeds said corresponding value of said first array by said second amount or by greater than said second amount, then incrementing said corresponding value by said second amount,
  C. if a sample of said odd beat is less than said corresponding value of said first array by said first amount but not said second amount, then decrementing said corresponding value by said first amount, and
  D. if a sample of said odd beat is less than said corresponding value of said first array by said second amount or by greater than said second amount, then decrementing said corresponding value by said second amount;

(iv) comparing samples of an even beat of said ECG data to corresponding values in said second array and adjusting said values of said second array as follows
  A. if a sample of said even beat exceeds said corresponding value of said second array by a first amount but by less than a second amount, then incrementing said corresponding value by said first amount,
  B. if a sample of said even beat exceeds said corresponding value of said second array by second amount or by greater than said second amount, then incrementing said corresponding value by said second amount,
  C. if a sample of said even beat is less than said corresponding value of said second array by said first amount but not said second amount, then decrementing said corresponding value by said first amount, and
  D. if a sample of said even beat is less than said corresponding value of said second array by said second amount or by greater than said second amount, then decrementing said corresponding value by said second amount; and (v) repeating steps (iii) and (iv) for a plurality of said odd and even beats of said ECG data.

11. The method of claim 10, wherein step (d) comprises:
calculating a difference between sample points of said odd median complex and sample points of said even median complex to obtain said estimate of the amplitude of beat-to-beat alternation in said ECG signal.

12. A system for quantifying alternation in an ECG signal having a plurality of beats, the method comprising the steps of:
means for receiving digitized ECG data representing the ECG signal;
means for calculating an odd median complex for at least one odd beat in said ECG data and for calculating an even median complex for at least one even beat in said ECG data; and
means for comparing said odd median complex with said even median complex to obtain an estimate of the amplitude of beat-to-beat alternation in said ECG signal.

13. The system of claim 12, further comprising:
means for filtering said ECG data.

14. The system of claim 12, wherein said comparing means comprises:
means for comparing a T-wave portion of said odd median complex with a T-wave portion of said even median complex to obtain an estimate of the amplitude of beat-to-beat alternation in said ECG signal.

15. The system of claim 12, wherein said calculating means comprises:
means for initializing a first array with a plurality of odd median complex values, said first array representing said odd median complex;
means for initializing a second array with a plurality of even median complex values, said second array representing said even median complex;
means for comparing samples of an odd beat of said ECG data to corresponding values in said first array and adjusting said values of said first array as follows
  if a sample of said odd beat exceeds said corresponding value of said first array by a first amount but by less than a second amount, then incrementing said corresponding value by said first amount,
  if a sample of said odd beat exceeds said corresponding value of said first array by said second amount or by greater than said second amount, then incrementing said corresponding value by said second amount,
  if a sample of said odd beat is less than said corresponding value of said first array by said first amount but not said second amount, then decrementing said corresponding value by said first amount, and
  if a sample of said odd beat is less than said corresponding value of said first array by said second amount or by greater than said second amount, then decrementing said corresponding value by said second amount; and means for comparing samples of an even beat of said ECG data to corresponding values in said second array and adjusting said values of said second array as follows if a sample of said even beat exceeds said corresponding value of said second array by a first amount but by less than a second amount, then incrementing said corresponding value by said first amount, if a sample of said even beat exceeds said corresponding value of said second array by said second amount or by greater than said second amount, then incrementing said corresponding value by said second amount, if a sample of said even beat is less than said corresponding value of said second array by said first amount but not said second amount, then decrementing said corresponding value by said first amount, and if a sample of said even beat is less than said corresponding value of said second array by said second amount or by greater than said second amount, then decrementing said corresponding value by said second amount.

16. The system of claim 12, wherein said comparing means comprises:

means for calculating a difference between sample points of said odd median complex and sample points of said even median complex to obtain said estimate of the amplitude of beat-to-beat alternation in said ECG signal.

17. A computer program product comprising a computer useable medium having computer program logic for enabling at least one processor in a computer system to quantify alternation in an ECG signal, said computer program logic comprising:

first means for enabling the at least one processor to receive digitized ECG data representing the ECG signal;

second means for enabling the at least one processor to calculate an odd median complex for at least one odd beat in said ECG data and to calculate an even median complex for at least one even beat in said ECG data; and third means for enabling the at least one processor to compare said odd median complex with said even median complex to obtain an estimate of the amplitude of beat-to-beat alternation in said ECG signal.

* * * * *